(12) United States Patent
Lundberg et al.

(10) Patent No.: US 8,956,296 B2
(45) Date of Patent: Feb. 17, 2015

(54) SYSTEMS AND METHODS FOR ACTIVE OPTIMIZED SPATIO-TEMPORAL SAMPLING

(75) Inventors: Andrew K. Lundberg, Woodinville, WA (US); Juin-Jet Hwang, Mercer Island, WA (US)

(73) Assignee: FUJIFILM SonoSite, Inc., Bothell, WA (US)

(*) Notice: Subject to any disclaimer, the term of this patent is extended or adjusted under 35 U.S.C. 154(b) by 391 days.

(21) Appl. No.: 12/277,124

(22) Filed: Nov. 24, 2008

(65) Prior Publication Data

US 2010/0130855 A1    May 27, 2010

(51) Int. Cl.
- A61B 8/00    (2006.01)
- G01S 7/52    (2006.01)
- G01S 15/89   (2006.01)

(52) U.S. Cl.
CPC .. *A61B 8/00* (2013.01); *A61B 8/469* (2013.01); *G01S 7/52085* (2013.01); *G01S 15/8995* (2013.01); *G01S 7/52063* (2013.01); *G01S 7/52077* (2013.01)
USPC ............ 600/437; 600/407; 600/447; 382/128

(58) Field of Classification Search
None
See application file for complete search history.

(56) References Cited

U.S. PATENT DOCUMENTS

| | | | |
|---|---|---|---|
| 4,649,927 A | 3/1987 | Fehr et al. | |
| 4,653,505 A | 3/1987 | Iinuma | |
| 5,301,674 A * | 4/1994 | Erikson et al. | 600/447 |
| 5,603,318 A | 2/1997 | Heilbrun et al. | |
| 6,123,670 A | 9/2000 | Mo | |
| 6,233,476 B1 | 5/2001 | Strommer et al. | |
| 6,317,621 B1 | 11/2001 | Graumann et al. | |
| 6,390,981 B1 * | 5/2002 | Jago | 600/443 |
| 6,490,477 B1 | 12/2002 | Zylka et al. | |
| 6,524,252 B1 | 2/2003 | Yu et al. | |
| 6,591,130 B2 | 7/2003 | Shahidi | |
| 6,708,055 B2 | 3/2004 | Geiser et al. | |
| 6,790,181 B2 | 9/2004 | Cai et al. | |
| 7,386,339 B2 | 6/2008 | Strommer et al. | |

(Continued)

FOREIGN PATENT DOCUMENTS

| | | |
|---|---|---|
| CN | 101231457 | 7/2008 |
| EP | 1950582 | 7/2008 |

OTHER PUBLICATIONS

U.S. Appl. No. 11/749,319, Lundberg et al.

(Continued)

*Primary Examiner* — Unsu Jung
*Assistant Examiner* — Michael N Fisher
(74) *Attorney, Agent, or Firm* — Perkins Coie LLP (57) ABSTRACT

Systems and methods which provide active optimized spatio-temporal sampling (AOSTS) for image generation are shown. Embodiments actively select one or more regions of interest (ROIs) in a multi-beam ultrasound sampling mode, to minimize temporal image artifacts in the ROIs and thereby provide AOSTS. Such selection of ROIs according to embodiments results in various multi-beam sampling parameters, such as the number of rays that are used, the spacing between the rays that are used, the width of the rays that are used, the sequence of the rays that are used, the angle of the rays that are used, etc., being selected to provide optimized spatio-temporal sampling with respect to the selected ROIs. Selection of ROIs according to embodiments may include selecting parameters such as position, size, shape, orientation, direction, rate of change, etc.

7 Claims, 6 Drawing Sheets

(56) References Cited

U.S. PATENT DOCUMENTS

| | | | |
|---|---|---|---|
| 2002/0165448 A1 | 11/2002 | Ben-Haim et al. | |
| 2003/0050557 A1 | 3/2003 | Susil et al. | |
| 2003/0092989 A1 | 5/2003 | Aichhorn et al. | |
| 2003/0130576 A1 | 7/2003 | Seeley et al. | |
| 2003/0135119 A1 | 7/2003 | Lee et al. | |
| 2004/0006266 A1* | 1/2004 | Ustuner et al. | 600/407 |
| 2005/0171429 A1* | 8/2005 | Mathew et al. | 600/437 |
| 2005/0288588 A1* | 12/2005 | Weber et al. | 600/447 |
| 2007/0055126 A1* | 3/2007 | Yu et al. | 600/407 |
| 2007/0073136 A1 | 3/2007 | Metzger | |
| 2007/0086606 A1* | 4/2007 | Goodwin | 381/116 |
| 2007/0100234 A1 | 5/2007 | Arenson et al. | |
| 2007/0167806 A1* | 7/2007 | Wood et al. | 600/459 |
| 2007/0193354 A1 | 8/2007 | Felix et al. | |
| 2007/0239020 A1* | 10/2007 | Iinuma et al. | 600/459 |
| 2007/0277611 A1* | 12/2007 | Portzgen et al. | 73/592 |
| 2008/0114255 A1 | 5/2008 | Schwartz et al. | |
| 2008/0119735 A1 | 5/2008 | Lin et al. | |
| 2008/0183079 A1 | 7/2008 | Lundberg | |
| 2008/0188752 A1 | 8/2008 | Randall et al. | |
| 2008/0221425 A1 | 9/2008 | Olson et al. | |
| 2008/0269610 A1 | 10/2008 | Burla et al. | |
| 2010/0121190 A1 | 5/2010 | Pagoulatos et al. | |

OTHER PUBLICATIONS

U.S. Appl. No. 12/269,663, Pagoulatos et al.

International Search Report issued for PCT/US2008/075367 dated Nov. 14, 2008, 9 pgs.

Carr, Jonathan, "Surface Reconstructing in 3D Medical Imaging", Department of Electrical Engineering, University of Canterbury, Christchurch, New Zealand, Feb. 1996, 214 pgs.

Von Ramm et al., "Beam Steering with Linear Arrays," Aug. 1983, IEEE Transactions on Biomedical Engineering, vol. BME-30, No. 8.

International Search Report and the Written Opinion issued for PCT/US2009/064093, dated Mar. 4, 2010, 8 pages.

First Office Action, Chinese Patent Application 200810006980.0, mailed by the State Intellectual Property Office of People's Republic of China on Jun. 29, 2011, 14 pages.

International Search Report and the Written Opinion issued for PCT/US2009/062976, dated Jan. 7, 2010, 11 pages.

Office Action dated Mar. 19, 2010 in U.S. Appl. No. 11/749,319, 7 pages.

Office Action dated Oct. 7, 2010 in U.S. Appl. No. 11/749,319, 9 pages.

Office Action issued Jun. 10, 2011 in U.S. Appl. No. 11/749,319, 11 pages.

United States Patent and Trademark Office Final Office Action, U.S. Appl. No. 11/749,319 of Andrew K. Lundberg, Jan. 26, 2012, 9 pages.

United States Patent and Trademark Office, Final Office Action, U.S. Appl. No. 11/749,319, mailed Apr. 4, 2014, 7 pages.

* cited by examiner

FIG. 7

SYSTEMS AND METHODS FOR ACTIVE OPTIMIZED SPATIO-TEMPORAL SAMPLING

CROSS-REFERENCE TO RELATED APPLICATIONS

The present application is related to U.S. patent application Ser. No. 11/749,319 entitled "System and Method for Optimized Spatio-Temporal Sampling," filed May 16, 2007, Ser. No. 12/269,663 entitled "Systems and Methods to Identify Interventional Instruments," filed Nov. 12, 2008, and to U.S. provisional patent application Ser. No. 60/886,877 entitled "System and Method for Temporal Coherence Spatial Sampling," filed Jan. 26, 2007, the disclosures of which are hereby incorporated by reference.

TECHNICAL FIELD

The invention relates to ultrasound imaging and more specifically to providing active optimized spatio-temporal sampling.

BACKGROUND OF THE INVENTION

Spatial compounding is a method of creating an ultrasound image by compiling multiple views or angles. Each view is obtained from multiple lines of sight at different angles. This is a departure from traditional ultrasound imaging that used a single line of sight. The views from the multiple angles are combined to create a single image, thereby reinforcing real-tissue information and suppressing random artifacts. Spatial compounding has resulted in a reduction in speckle noise artifacts; shadowing artifacts and image-degrading artifacts. In addition, such compounding, which is also known as compound imaging, results in improvements in: contrast resolution; needle visualization; tissue contrast resolution; fine-structure delineation; interface/border continuity and lateral edge detection.

The original literature called this technique Compound Imaging. Many companies are now using this technique calling it various names including: SonoCT; CrossBeam Imaging; and Spatial Compounding.

Some systems use a method where information from both the transmit and the receive beam steering is processed to produce images from multiple view angles. The multiple images are aligned and combined to form an image. Images that are created using both transmit and receive information are typically superior to images consisting of receive information only.

One drawback of the compounding methods now employed is that they result in temporal artifacts being introduced into the final image which, in turn, causes ambiguity to the user.

BRIEF SUMMARY OF THE INVENTION

The present invention is directed to systems and methods which provide active optimized spatio-temporal sampling (AOSTS) for image generation. Optimized spatio-temporal sampling (OSTS) is accomplished according to embodiments by selecting multi-beam sampling parameters, such as selecting the order of steered and straight rays fired within a frame, to provide optimized sampling in association with a portion of an imaged volume. For example, optimized spatio-temporal sampling may be accomplished by changing the multi-beam firing sequence so that a portion of an imaged volume is sampled in subsequent rays or beams (as opposed to subsequent frames) to thereby provide a location of minimal temporal sampling difference at the portion of the imaged volume.

Embodiments of the invention actively select one or more regions of interest (ROIs) in a multi-beam ultrasound sampling mode, to minimize temporal image artifacts in the ROIs caused by image generation techniques such as spatial compounding process for example, and thereby provide AOSTS. Such selection of ROIs according to embodiments results in various multi-beam sampling parameters, such as the number of rays that are used, the spacing between the rays that are used, the width of the rays that are used, the sequence of the rays that are used, the angle of the rays that are used, etc., being selected to provide OSTS with respect to the selected ROIs. Embodiments of the invention may additionally or alternatively provide for various multi-beam sampling parameters being directly selected, such as to manually configure an OSTS operation, to adapt an OSTS operation for a particular attribute, etc. and thereby provide AOSTS.

Selection of ROIs according to embodiments of the invention may include selecting ROI parameters in addition to or in the alternative to a position of an ROI. For example, ROI selection parameters may include position, size, shape, orientation, direction, rate of change, etc. Accordingly, a ROI of a particular size, at an identified location, moving in an indicated direction, at a particular rate may be selected according to embodiments of the invention. Thereafter, OSTS may be provided with respect to the ROI thus providing AOSTS of an embodiment of the invention.

Selection of ROIs and/or selecting multi-beam sampling parameters for OSTS operation (collectively selection of AOSTS parameters) may be accomplished automatically, manually, or a combination thereof according to embodiments of the invention. For example, an ultrasound imaging system adapted according to embodiments of the invention may operate to automatically or semi-automatically select one or more AOSTS parameter based upon a current mode of operation, an imaging technique being utilized, a procedure being performed, a particular user or user type operating the system, a type of transducer being used, an object or feature present in a generated image, a selected imaging attribute (e.g., focal depth), an image zoom level selected, etc. Additionally or alternatively, a user may select one or more AOSTS parameter through the use of an ultrasound imaging system user interface, such as may comprise pointer input, touch screen input, alphanumeric input, audio input, etc.

Irrespective of whether AOSTS parameters are provided automatically or manually, embodiments of the invention operate to optimize imaging to create a customized solution for particular situations, procedures, modes of operations, applications, etc. As different imaging needs are identified embodiments of the invention operate to modify AOSTS parameters for continued optimized imaging.

AOSTS of embodiments of the present invention provides for OSTS being implemented with respect to strategic portions of a generated image. Accordingly, rather than applying OSTS with respect to a default location within a sampled volume, such as the middle of the image as would be the case with simple mixing of the order of steered and straight rays fired within a frame, selected portions of an imaged volume are provided the benefits of OSTS using AOSTS techniques of the present invention. Moreover, embodiments of the present invention provide AOSTS to achieve optimized sampling based on application specific needs.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWING

For a more complete understanding of the present invention, reference is now made to the following descriptions taken in conjunction with the accompanying drawing, in which.

DETAILED DESCRIPTION OF THE INVENTION

Figure 1:
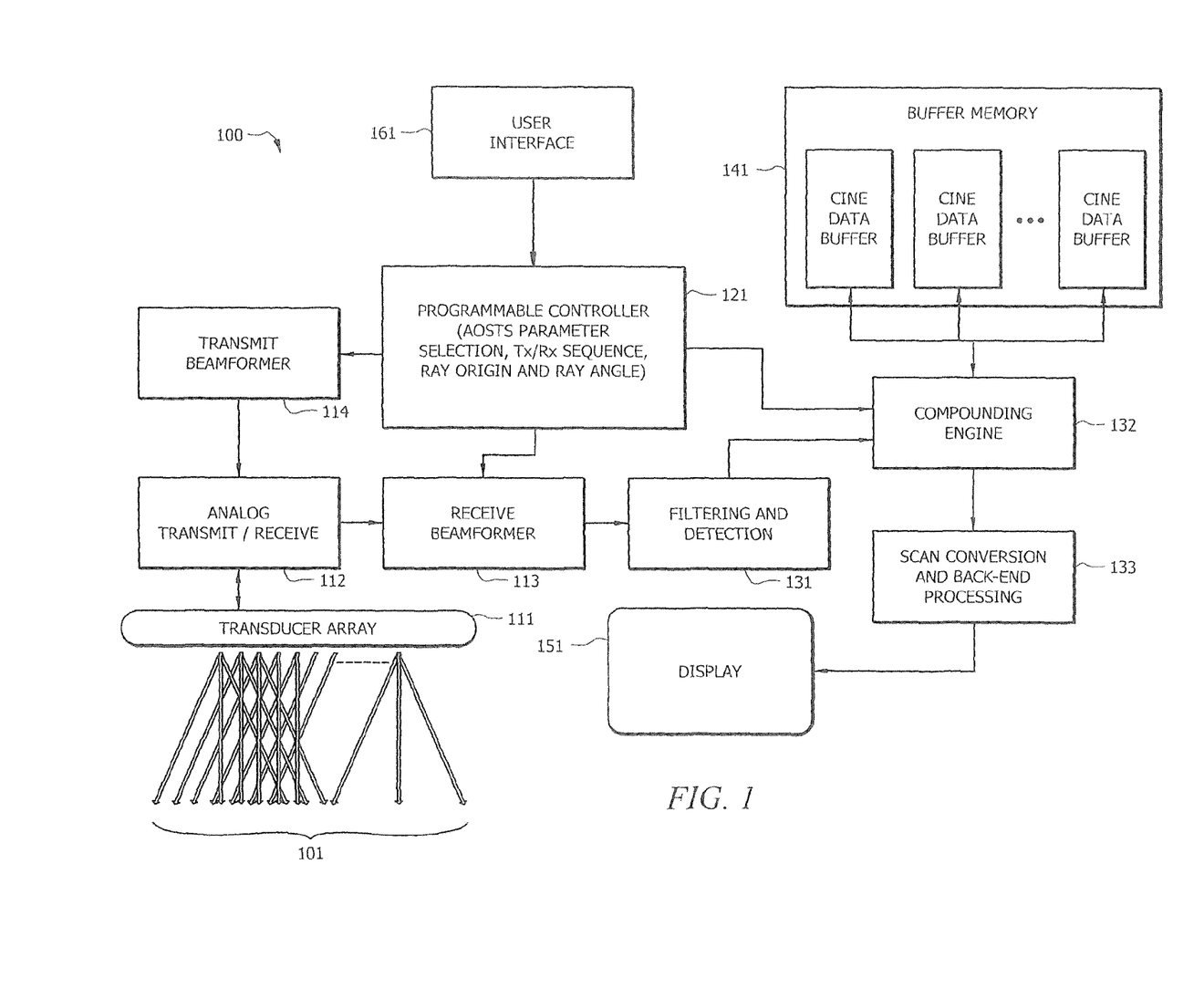
FIG. 1 shows a system adapted to provide active optimized spatio-temporal sampling according to an embodiment of the invention.

Directing attention to FIG. 1, system 100 adapted to provide AOSTS image processing according to embodiments of the invention is shown. To aid in understanding the concepts of the present invention, system 100 will be described herein with reference to an ultrasound imaging system, such as may comprise a diagnostic ultrasound system utilized with respect to medical examinations and/or performing medical procedures. However, it should be appreciated that concepts of the present invention are applicable to other imaging modalities, such as computer aided tomography (CAT), magnetic resonance imaging (MRI), X-ray imaging, etc.

In operation, controller 121 controls transmission and reception of sampling signals for imaging operations. In the illustrated embodiment, controller 121 operates with transmit beamformer 114, transmit/receive circuitry 112, and transducer array 111 to generate one or more of rays 101 for signal transmission and transducer array 111, transmit/receive circuitry 112, and receive beamformer 113 to generate one or more rays 101 for received signals. Transducer array 111 may comprise various transducer array configurations, such as phased arrays, curved arrays, linear arrays, one, two, and three-dimensional arrays, etc., according to embodiments of the invention.

Controller 121 may comprise one or more processors, such as a central processing unit (CPU), programmable gate array (PGA), application specific integrated circuit (ASIC), etc., operating under control of an instruction set providing operation as described herein. Controller 121 may additionally comprise processor or computer readable media, such as random access memory (RAM), read only memory (ROM), magnetic memory, optical memory, etc., for storing instruction sets, operating parameters, and/or other useful data. Controller 121 of embodiments, operable under control of an instruction set, generates the transmit ray sequence and ray parameters (e.g., steerage angle, beam width, etc.) for providing active optimized spatiotemporal sampling (AOSTS) insonification of a volume in conjunction with transmit beamformer 114 and transmit/receive circuitry 112. Likewise, controller 121 of embodiments generates the receive ray sequence and ray parameters for AOSTS signal receiving in conjunction with transmit/receive circuitry 112 and receive beamformer 113.

The output of transmit/receive circuitry 112 of the illustrated embodiment supplies transmit signals to transducer array 111. In accordance with control provided by controller 121, the output from transducer array 111 is a sequence of rays or beams which are used for forming an image by collecting signals "bouncing" back from a target within a volume. As one example, there are a plurality of rays (e.g., 128 rays) for each steer angle in each time differentiated frame. The returned signal for each fired ray is received by transducer array 111 and communicated via transmit/receive circuitry 112 (e.g., analog receiver circuitry of transmit/receive circuitry 112) to receive beamformer 113. The output of receive beamformer 113 is a beamformed ray (e.g., a digitally sampled and beamformed ray) formed in accordance with ray parameters of a selected set of multi-beam sampling parameters.

The rays output by receive beamformer 113 are provided to filtering and detection circuitry 131 for further signal processing, such as filtering, object detection, etc., according to the illustrated embodiment. Ray signals processed by filtering and detection circuitry 131 are provided to compounding engine 132 for compounding to create an ultrasound image by compiling multiple views or angles. In operation according to embodiments, collections of similarly steered rays are aligned, scan converted into a common grid and buffered by compounding engine 132 and stored in buffer memory 141. When enough data is present to compound (or combine) the data from different steers, compounding engine 132 compounds data stored in buffer memory 141, such as by computing a weighted average for each common sample in the buffer memory for the given frame of ultrasound data, for image generation. The compounded data is then provided by compounding engine 132 of the illustrated embodiment to scan converter and back-end processing 133 for processing to provide image display on display 151.

User interface 161 may comprise any of a number of input and output devices useful for accepting data input, control parameters, operating instructions, etc. and/or outputting data, reports, status indicators, error messages, alarms, images, etc. For example, user interface 161 of embodiments may comprise a keyboard, a pointer (e.g., mouse, digitizing tablet, touch pad, joystick, trackball, touch screen interface, etc.), a microphone, a speaker, a display, and/or the like. It should be appreciated that user interface 161 may comprise display 151 according to embodiments of the invention.

AOSTS operation selects multi-beam sampling parameters to provide optimized sampling in association with one or more "region of interest" (ROI) within an image volume (e.g., a portion of a human body or other target substance being insonified for ultrasound image generation). Accordingly, selection of ROIs according to embodiments results in various multi-beam sampling parameters, such as the number of rays that are used, the spacing between the rays that are used, the width of the rays that are used, the sequence of the rays that are used, the angle of the rays that are used, the trajectory along which the image is to be optimized, etc., being selected. The selection of ROIs and/or selecting multi-beam sampling parameters for OSTS operation is collectively referred to herein as selection of AOSTS multi-beam sampling parameters or AOSTS parameters. Accordingly, selection of AOSTS parameters according to embodiments of the invention may include selecting parameters in addition to or in the alternative to a position of an ROI. For example, AOSTS parameters may include position, size, shape, orientation, direction, rate of change, etc. For example, a ROI of a particular size, at an identified location, moving in an indicated direction, at a particular rate may be selected according to embodiments of the invention.

Various AOSTS parameters may be selected through use of algorithms or other automated means which select parameters and/or operator input for direct selection, such as to manually configure an OSTS operation, to adapt an OSTS operation for a particular attribute, etc. and thereby provide AOSTS. Accordingly, selection of AOSTS parameters may be accomplished automatically, manually, or a combination thereof according to embodiments of the invention.

In operation according to embodiments of the invention, controller 121 implements an algorithm or algorithms as part of its instruction set which automatically or semi-automatically selects one or more ROI based upon a current mode of operation, an imaging technique being utilized, a procedure being performed, a particular user or user type operating the system, a type of transducer being used, an object or feature present in a generated image, a selected imaging attribute, an image zoom level selected, etc. For example, when a user selects a color Doppler mode and places a Doppler color box over a portion of an image, an algorithm implemented by controller 121 may recognize the mode selected and select an ROI within the Doppler color box. As another example, when a user is performing a particular procedure, such as to measure intima-media thickness (IMT), an algorithm implemented by controller 121 may select an ROI corresponding to an area within the image associated with the wall of the carotid artery. ROIs may be selected automatically or semi-automatically based upon other information, such as the focal depth, the typical location or relationship of relevant structure within an image or for a procedure, the typical movement rate and/or direction of relevant structure, analysis of one or more objects appearing in an image, etc.

Embodiments of the present invention may utilize techniques to automatically or semi-automatically identify relevant structure (and thus an ROI) and track the movement of such structure (and thus update the R01). For example, the techniques shown and described in the above referenced patent application entitled "Systems and Methods to Identify Interventional Instruments" for identifying relevant structure and for tracking such structure may be utilized in ROI selection and/or updating according to embodiments of the invention.

Additionally or alternatively, a user may select one or more AOSTS parameter through operation of user interface 161 according to embodiments of the invention. For example, a user may use a pointing device to point to an area or object of interest within an image to select a ROI. Such a user may select a point, an area (e.g., using a "rubber band box," "lasso," etc.), a structure, a region, a plane, etc.

Irrespective of whether AOSTS parameters are provided automatically or manually, system 100 of embodiments operates to optimize imaging with respect to one or more selected ROIs. For example, controller 121 of embodiments operates to establish the number of rays that are to be used, the spacing between the rays that are to be used, the width of the rays that are to be used, the sequence of the rays that are to be used, the angle of the rays that are to be used, the width of the rays to be used, and/or the like in accordance with the selected ROIs.

As different imaging needs are identified or as changes are identified with respect to an image (e.g., movement of a ROI, different imaging modes are selected, imaging parameters are changed, etc.) algorithms operable with respect to controller 121 preferably operate to modify AOSTS parameters for continued optimized imaging. For example, where an ROI is identified in association with a focal depth, as the focal zone is moved embodiments of the invention track those adjustments and change AOSTS parameters based on the updated location of the focal zone. If an operator invokes a zoom box that is in region of the image different than currently selected ROIs, embodiments automatically adjust AOSTS parameters to provide spatio-temporal sampling based on the zoom box. Similarly, if an operator changes the sector size (e.g., to use a sector scan head), embodiments adjust AOSTS parameters accordingly. For example, embodiments use a less steep ray angle with respect to a tighter field of view and the ray angles may be adjusted as the sector width is changed. Any of the foregoing AOSTS parameters or other AOSTS parameters may additionally or alternatively be manually selected or adjusted by an operator.

Figure 2:
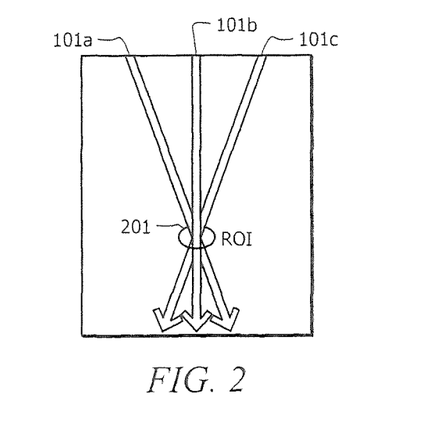
FIG. 2 shows a representation of ray interleaved spatial compounding with active optimized spatio-temporal sampling implemented according to an embodiment of the invention.

FIG. 2 shows a simplified representation of ray interleaved spatial compounding with AOSTS implemented according to an embodiment of the invention. According to an embodiment, data is collected for all "look" angles in one frame sequence, with the ray firing sequence and origins (ordinate location of the beam as it leaves the scan head) of rays 101a-101c being optimized so that the time between subsequent samples from different look angles is minimized in ROI 201, wherein ROI 201 is selected as described above. For example, for a 128 line frame, rays are fired in sequence A, B, C (A=steer right, B=steer straight, C=steer left), but the ray origins are modified by the time difference of the starting point (origin positions) so that the temporal difference is minimized in ROI 201. In this example there are a total of 384 rays fired. Once the frame containing all look angles is collected, the data is compounded (combined) into a single frame of data. When using this method, the time to collect the data in the ROI is close to the time of flight for two rays plus the time of flight to ROI 201. This technique minimizes motion artifacts in the selected ROI or ROIs.

It should be appreciated that the illustration of FIG. 2 is provided to illustrate the concepts herein, and thus embodiments of the invention are not limited to the particular number of rays, ray geometries, ray angles, ray firing order, ROI location, number of ROIs, etc. For example, although the embodiment of FIG. 2 illustrates substantially symmetric ray angles, embodiments of the invention may utilize rays of asymmetric angles and/or different origin locations in providing active optimized spatio-temporal sampling. Likewise, the order of the rays fired (e.g., steered and/or straight) within a frame can be mixed so as to create a desired spatio-temporal sample. Accordingly, embodiments of the invention may vary the number of rays that are fired, the spacing between the different rays that are fired, the sequence rays are fired in, the angle of each one of the rays, etc. for one or more selected ROI in providing active optimized spatio-temporal sampling.

Figure 2A:
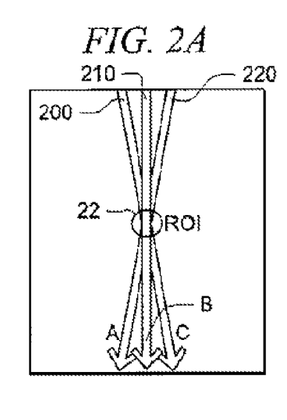
FIGS. 2A through 2C show embodiments of interleaved spatial compounding according to the inventive concepts taught herein.
Figure 2B:
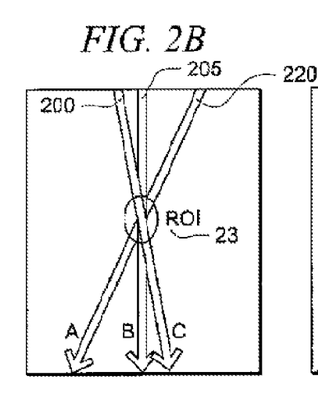
Figure 2C:
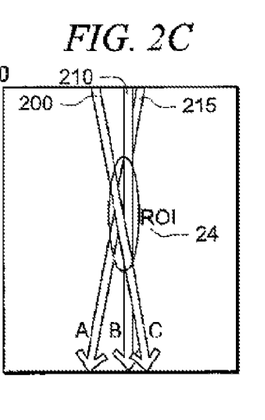

FIGS. 2A through 2C show embodiments of ray interleaved spatial compounding according to the inventive concepts taught herein. FIG. 2A shows one embodiment of ray interleaved spatial compounding with optimized temporal spatial sampling. In this embodiment, data is collected for all "look" angles in one frame sequence, with the ray firing sequence and origins (ordinate location of the beam as it leaves the scan head) being optimized so that the time between subsequent samples from different look angles is minimized in a desired region of interest, such as ROI 22. For example, for a 128 line frame, rays are fired in sequence A, B, C (A=steer left, B=steer straight, C=steer right), but the ray origins are modified by the time difference of the starting point as reflected by the numbers 200, 210 and 220 which correspond to origin positions so that the temporal difference is minimized in the ROI. In this example there are a total of 384 rays fired. Once the frame containing all look angles is collected, the date are compounded (combined) into a single frame of data. When using this method, the time to collect the data in the ROI is close to the time of flight for two rays plus the time of flight to ROI 22. This method minimizes motion artifacts in the ROI region.

FIG. 2B is a variation of FIG. 2A illustrating how the ray origin (shown by ray B originating from point 205 instead of from point 210 (as shown in FIG. 2A) can be modified to optimize the temporal sampling at ROI 23 with rays of asymmetric angles.

FIG. 2C shows one embodiment of ray interleaved spatial compounding with optimized temporal spatial sampling for an expanded ROI, such as ROI 24, using asymmetric spacing of the rays. It is possible, by varying either the position along the scan head a ray is fired from and/or the angle of the fired ray, to modify the ROI. The changing of the ROI then can be used in some procedures, for example, when tracking the insertion through a body of a needle, the ROI can be changed to coincide with the movement of the needle or other medical probe. In this manner the caregiver can keep the end (or other portion) of the probe in 44view". Also, by focusing on multiple ROI's, such as on the probe tip and the target, the trajectory of the probe is precisely adjustable.

As shown in FIGS. 2A, 2B and 2C, the order of steered and straight (steered straight) rays fired within a frame can be mixed so as to create the desired spatial sample. An example of a frame of this type would be made up of loops such as the following:

1) A loop of steered left rays;
2) A loop of steered left rays and steered straight rays;
3) A loop of steered left rays, steered right rays and steered straight rays;
4) A loop of steered right rays and steered straight rays;
5) A loop of steered right rays.

The length of loops 1, 2, 4 and 5 are defined, in one embodiment, by equation (1):

$$\text{Loop Length round(tan(steer angle)*screen depth/2)/pitch)*line density} \quad 1)$$

The length of loop 3 is defined, in one embodiment, by equation (2):

$$\text{Inner Loop Length=(Total elements*line density)}-2*\text{Loop Length} \quad 2)$$

One particular use for an improved image created by the above-described method is for anesthesia applications as well as for other high quality, artifact free, imaging applications where precise imaging is of prime importance.

As shown in FIG. 2A, rays 200, 210 and 220 (numbered to reflect origin positions) are fired in sequence and steered such that they are least temporally different in the target region, such as region 22. Region 22 can be a point or a region of interest depending on the relative steerage angles of rays 200, 210 and 220 as discussed above. While in the embodiments shown only three rays are shown forming a convergence, any number of rays, including all of the rays in the frame, can be used to define the optimized temporal difference range. In one embodiment, the angle of the steered rays can be adjusted and in other embodiments the sequence of ray origins (or a combination of sequence and angle) can be adjusted.

FIGS. 3-10 provide exemplary flow diagrams, such as may be performed using system 100 described above, showing selection of various AOSTS parameters according to embodiments of the invention. The embodiments of FIGS. 3-10 provide exemplary flow diagrams showing operator (manual) selection of various AOSTS parameters and system (automatic) selection of various AOSTS parameters. It should be appreciated that processing in accordance with various ones of the flow diagrams may be implemented throughout an imaging session, such as in response to corresponding events (e.g., user input, imaging mode selection, feature selection, etc.). Moreover, operation in accordance with the various of the illustrated flow diagrams may be combined for providing AOSTS in accordance with embodiments of the invention.

Figure 3:
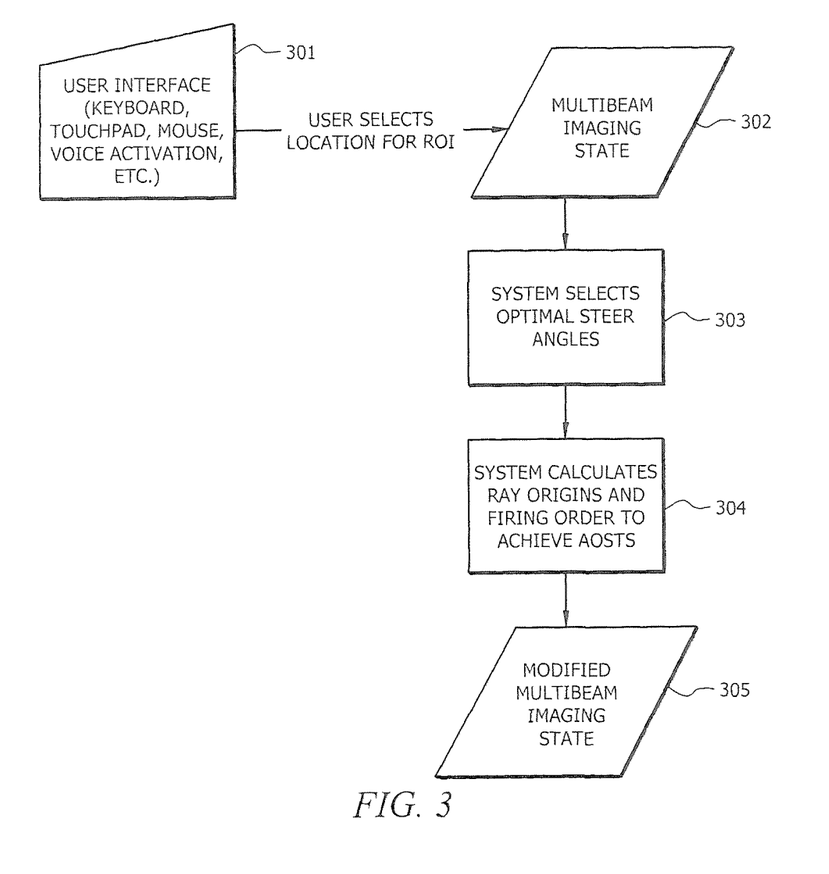
FIGS. 3-10 show flow diagrams for providing selection of various AOSTS parameters according to embodiments of the invention.

Directing attention to FIG. 3, manual selection of a ROI location is shown according to an embodiment of the invention. In the illustrated embodiment, a user manipulates user interface 301, such as may comprise a keyboard, a touch pad, a mouse, voice activation, etc., to select where a ROI for AOSTS operation is to be. Thereafter, the selected ROI location is provided to multi-beam imaging state 302. At block 303 optimal ray steer angles for the ROI are selected. New ray origins and ray firing order are calculated to achieve optimized spatio-temporal sampling with respect to the ROI at block 304. Thereafter, these AOSTS parameters are utilized to provide modified multi-beam imaging state 305. Modified multi-beam imaging state 305 thus operates to provide active optimized spatio-temporal sampling which is optimized with respect to the ROI location selected by the user.

Figure 4:
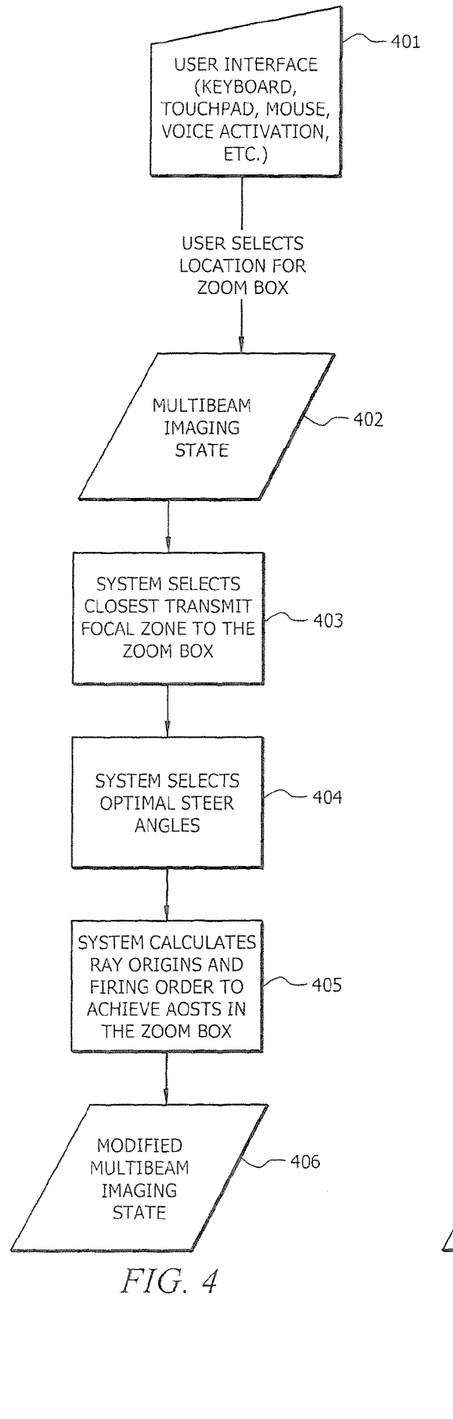

Referring now to FIG. 4, ROI selection linked to manual zoom box selection is shown according to an embodiment of the invention. In the illustrated embodiment, a user manipulates user interface 401, such as may comprise a keyboard, a touch pad, a mouse, voice activation, etc., to select a zoom box location and size. Thereafter, the selected zoom box information is provided to multi-beam imaging state 402. At block 403 a transmit focal zone closest to the zoom box location is selected as a ROI. At block 404 optimal ray steer angles for the ROI are selected. New ray origins and ray firing order are calculated to achieve optimized spatio-temporal sampling with respect to the ROI at block 405. Thereafter, these AOSTS parameters are utilized to provide modified multi-beam imaging state 406. Modified multi-beam imaging state 406 thus operates to provide active optimized spatio-temporal sampling which is optimized with respect to an ROI linked to a zoom box selected by the user.

Figure 5:
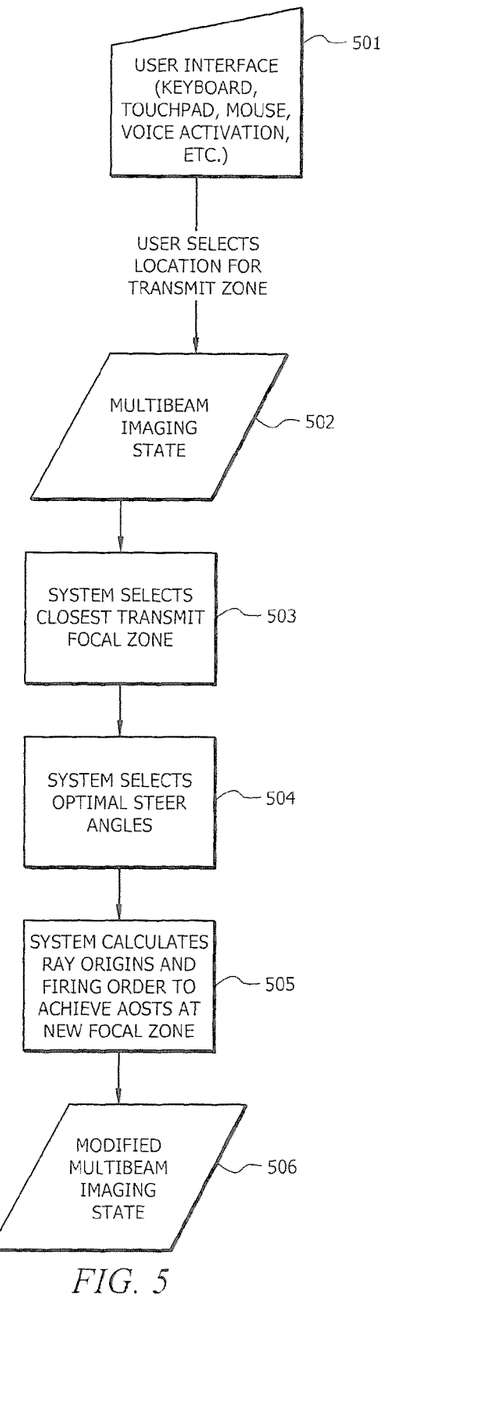

FIG. 5 shows ROI selection linked to manual focal zone movement according to an embodiment of the invention. In the illustrated embodiment, a user manipulates user interface 501, such as may comprise a keyboard, a touch pad, a mouse, voice activation, etc., to select a transmit zone. Thereafter, the selected transmit zone information is provided to multi-beam imaging state 502. At block 503 a transmit focal zone closest to the selected transmit zone is selected as a ROI. At block 504 optimal ray steer angles for the ROI are selected. New ray origins and ray firing order are calculated to achieve optimized spatio-temporal sampling with respect to the ROI at block 505. Thereafter, these AOSTS parameters are utilized to provide modified multi-beam imaging state 506. Modified multi-beam imaging state 506 thus operates to provide active optimized spatio-temporal sampling which is optimized with respect to an ROI linked to a transmit zone selected by the user.

Figure 6:
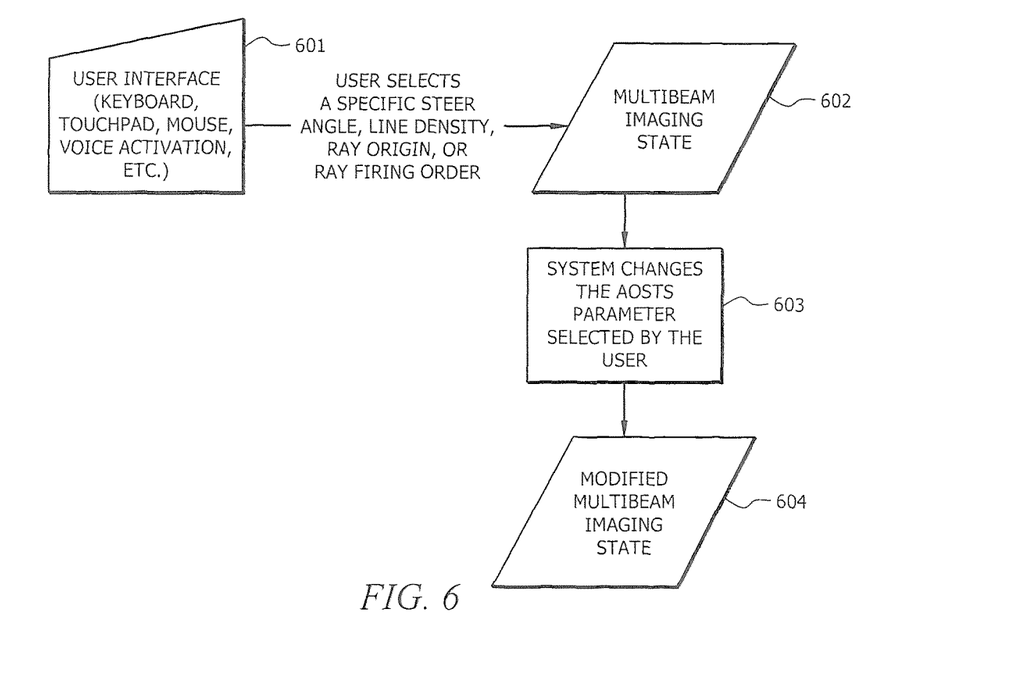

FIG. 6 shows manual AOSTS parameter selection according to an embodiment of the invention. In the illustrated embodiment, a user manipulates user interface 601, such as may comprise a keyboard, a touch pad, a mouse, voice activation, etc., to select one or more AOSTS parameters, such as steer angle, ray density, ray origin, ray firing order, etc. Thereafter, the selected AOSTS parameter or parameters are provided to multi-beam imaging state 602. At block 603 the system changes the AOSTS parameter(s) selected by the user. Thereafter, these AOSTS parameters are utilized to provide modified multi-beam imaging state 604. Modified multi-beam imaging state 604 thus operates to provide active optimized spatio-temporal sampling which is optimized with respect to AOSTS parameters directly selected by the user.

Figure 7:
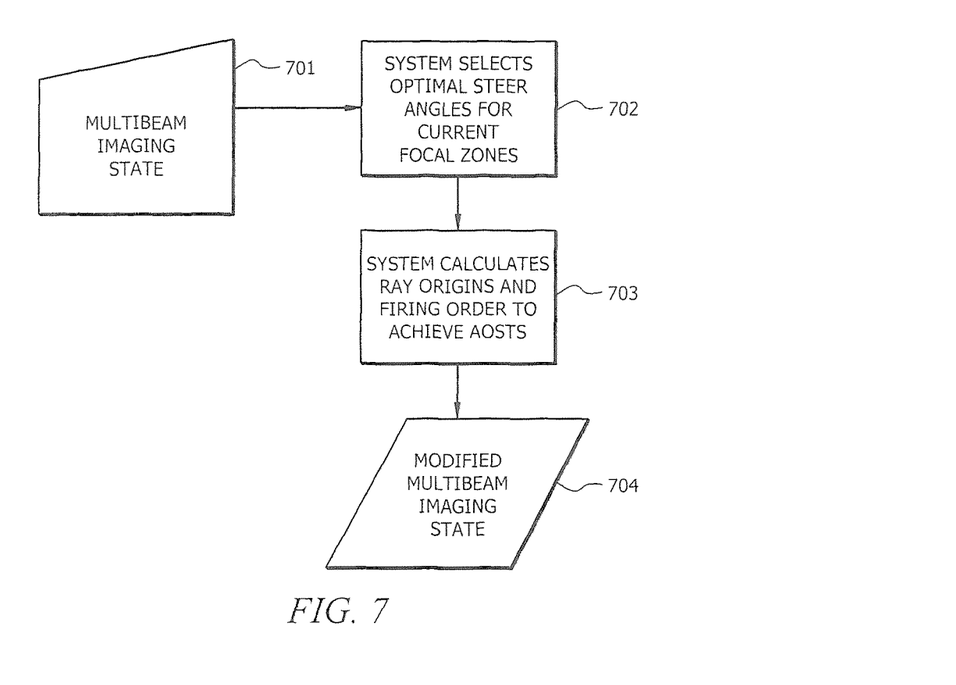

Referring now to FIG. 7, ROI selection linked to current focal zones is shown according to an embodiment of the invention. In the illustrated embodiment, multi-beam imaging state 701 is invoked. At block 702 optimal ray steer angles for current transmit focal zones are selected. New ray origins and ray firing order are calculated to achieve optimized spatio-temporal sampling with respect to the focal zones at block 705. Thereafter, these AOSTS parameters are utilized to provide modified multi-beam imaging state 704. Modified multi-beam imaging state 704 thus operates to provide active optimized spatio-temporal sampling which is optimized with respect to current focal zones.

Figures 8, 9, 10:
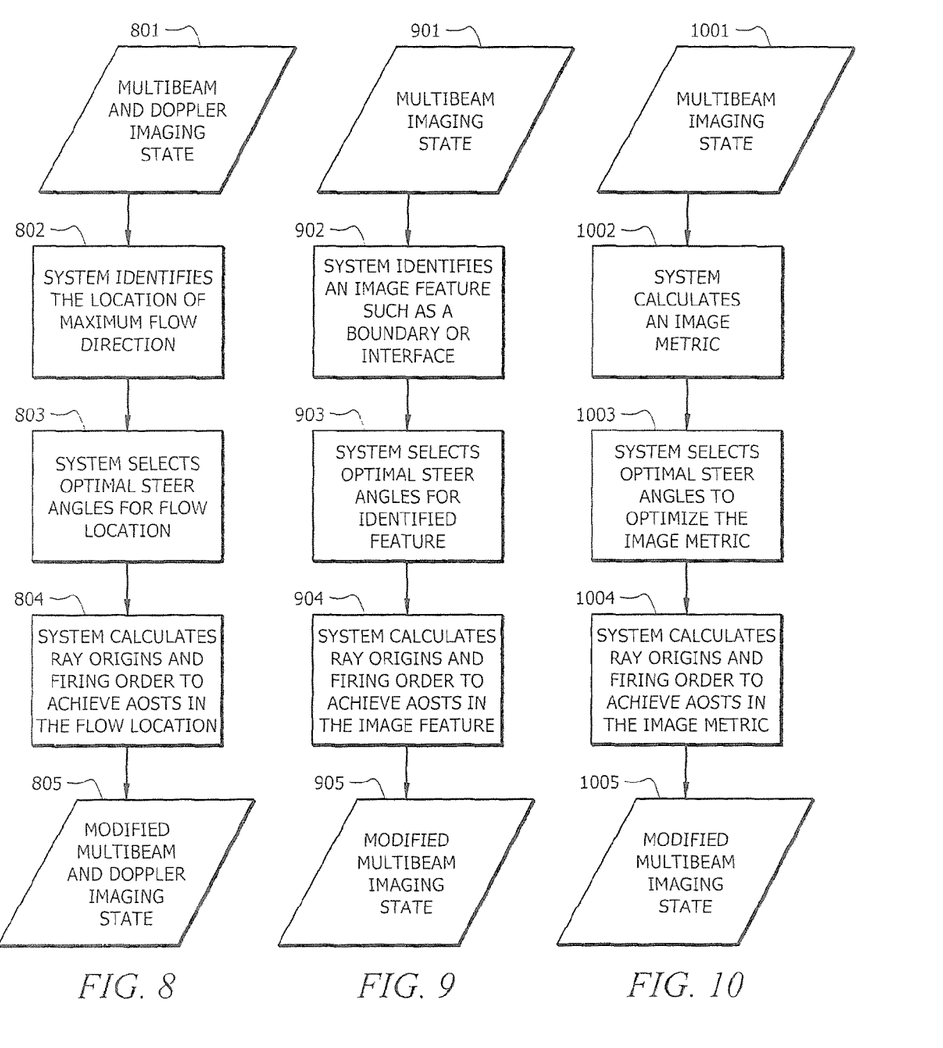

FIG. 8 shows automatic ROI selection linked to measured Doppler flow according to an embodiment of the invention. In the illustrated embodiment, multi-beam imaging state 801 is invoked. At block 802 the system operates to identify the location and/or direction of maximum flow. At block 803 optimal ray steer angles for the maximum flow are selected. It should be appreciated that operation according to FIG. 8 may select an optimal angle for visualizing the region for the identified flow location. New ray origins and ray firing order are calculated to achieve optimized spatio-temporal sampling with respect to the maximum flow at block 804. Thereafter, these AOSTS parameters are utilized to provide modified multi-beam imaging state 805. Modified multi-beam imaging state 805 thus operates to provide active optimized spatio-temporal sampling which is optimized with respect to a maximum flow, or some other flow characteristic/metric.

It should be appreciated that utilization of Doppler flow imaging modes are often used with respect to living vascular systems. Thus the use of color Doppler to show flow is often associated with structure which is pulsating (e.g., expanding and contracting), such as with the beat of a heart. Accordingly, spatial compounding has heretofore resulted in relatively poor quality images because of the movement of image features, such as vascular walls, between the time the various rays used to compound a portion of the image are fired. For example, a pulsating vessel in a typical implementation of spatial compounding appears poorly defined in a generated image (e.g., definitions of the border of the vessel are very poor) because the vessel has changed shape between the various ray steered frames. However, operation in accordance with the embodiment of FIG. 8 by selecting the ROI at such a location the generated image will provide a more clear image because the rays that are compounded for that ROI are fired to minimize temporal differences, and thus physical differences of the subject structure due to pulsating or other movement.

FIG. 9 shows automatic ROI selection linked to detected image features according to an embodiment of the invention. In the illustrated embodiment, multi-beam imaging state 901 is invoked. At block 902 the system operates to detect an image feature, such as a particular structure, boundary, interface, etc. For example, techniques shown and described in the above referenced patent application entitled "Systems and Methods to Identify Interventional Instruments" may be utilized to detect one or more image feature. At block 903 optimal ray steer angles for the detected feature are selected. New ray origins and ray firing order are calculated to achieve optimized spatio-temporal sampling with respect to the detected feature at block 904. Thereafter, these AOSTS parameters are utilized to provide modified multi-beam imaging state 905. Modified multi-beam imaging state 905 thus operates to provide active optimized spatio-temporal sampling which is optimized with respect to a feature detected in the image.

FIG. 10 shows automatic ROI modified in accordance with a compounding quality metric or regional motion metric. In the illustrated embodiment, multi-beam imaging state 1001 is invoked. At block 1002 the system operates to calculate an image metric, such as an alignment of compounding overlap, sharpness of a feature over time, a regional motion metric, a minimum image frame rate, a minimum spatial resolution, a number of lines to be used, or other quality of image metric. At block 1003 optimal ray steer angles for the image metric are selected. New ray origins and ray firing order are calculated to achieve optimized spatio-temporal sampling with respect to the image metric at block 1004. Thereafter, these AOSTS parameters are utilized to provide modified multi-beam imaging state 1005. Modified multi-beam imaging state 1005 thus operates to provide active optimized spatio-temporal sampling which is optimized with respect to image quality metrics.

A particular ROI for which AOSTS is provided according to embodiments of the invention may be of various sizes and shapes. Size and shape of an ROI may be selected automatically, manually, or a combination. For example, once a ROI is identified in accordance with operation of a processing flow set forth above, a user may manually define or adjust the size and/or shape of the ROI, such as using a pointing device, a "rubber band box," a "lasso," etc. Likewise, once a ROI is identified in accordance with operation of a processing flow set forth above, controller 121 operating under control of an algorithm there of may automatically define or adjust the size and/or shape of the ROI, such as by identifying structure within the image, identifying a boundary within the image, selecting a region within the image, selecting a plane within the image, etc.

Embodiments of the invention may operate to implement AOSTS for a particular size or shape of ROI by changing the ray firing order, ray origin location, and/or ray firing angle. For example, embodiments may operate to utilize steep or acute ray firing angles to provide AOSTS with respect to a small area. Correspondingly, less steep or less acute ray firing angles may be used to provide AOSTS with respect to a larger area.

It should be appreciated that operation according to the foregoing embodiments provides improved image quality in one or more regions that are important or are of particular interest to a user. For example, areas that are the focus of the users' attention are automatically identified and AOSTS provided for image quality enhancement provided with respect thereto according to embodiments of the invention. These areas are preferably updated or changed as areas that are the focus of the users' attention change, such as through repeated operation of the processing flows set forth above.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A system comprising:
    a transducer adapted to form sampling rays for image generation;
    a processor;
    a non-transitory computer-readable storage medium storing instructions executable by the processor, the instructions including:
        instructions for configuring the processor to:
            receive an identification of a region of interest within a target volume;
            determine asymmetric ray angles for two or more frames of sampling rays that are to be fired from positions along the transducer;
            fire the sampling rays in an order and from positions on the transducer such that the paths of the sampling rays intersect at a plurality of points having different depths within an expanded region of interest that includes the received region of interest, wherein the positions, asymmetric angles and order of the sampling rays are selected to minimize a time between subsequent samples from different look angles in the expanded region of interest; and
    a compounding engine configured to collect data based on said fired sampling rays for each of the frames and compound said data to generate a compounded image including said expanded region of interest.

2. The system of claim 1, wherein the non-transitory computer-readable storage medium further stores instructions for rendering a user interface operable to receive information from a user input to identify said region of interest.

3. The system of claim 1, wherein the non-transitory computer-readable storage medium further stores instructions for rendering a user interface operable to display a zoom box in a previously rendered image and receive an input from an operator selecting an area within said zoom box as said region of interest.

4. The system of claim 1, wherein the non-transitory computer-readable storage medium further stores instructions for rendering a user interface for receiving a selection of a focal zone as said region of interest.

5. The system of claim 4, wherein the non-transitory computer-readable storage medium further stores instructions for automatically selecting said region of interest as a function of said focal zone.

6. The system of claim 1, wherein the non-transitory computer-readable storage medium further stores instructions for invoking a flow measurement with respect to a previously rendered image, and automatically selecting said region of interest as a function of said flow measurement.

7. The system of claim 1, wherein the non-transitory computer-readable storage medium further stores instructions for:
    identifying a feature for detection;
    detecting an area of a previously rendered image volume associated with said identified feature; and
    automatically selecting said region of interest in said target volume.

\* \* \* \* \*